US008778027B2

(12) United States Patent
Medina

(10) Patent No.: US 8,778,027 B2
(45) Date of Patent: *Jul. 15, 2014

(54) IMPLANT APPARATUS AND METHOD INCLUDING TEE AND SCREW MECHANISM FOR SPINAL FUSION

(75) Inventor: Mark Patrick Medina, Torrance, CA (US)

(73) Assignee: Medevice IP Holdings, LLC, Albuquerque, NM (US)

(*) Notice: Subject to any disclaimer, the term of this patent is extended or adjusted under 35 U.S.C. 154(b) by 134 days.

This patent is subject to a terminal disclaimer.

(21) Appl. No.: 13/438,117

(22) Filed: Apr. 3, 2012

(65) Prior Publication Data

US 2013/0190877 A1    Jul. 25, 2013

Related U.S. Application Data

(60) Provisional application No. 61/589,500, filed on Jan. 23, 2012.

(51) Int. Cl.
*A61F 2/44* (2006.01)

(52) U.S. Cl.
USPC ...................................................... 623/17.16

(58) Field of Classification Search
CPC ....... A61F 2/44; A61F 2/4455; A61F 2/4611; A61F 2002/30637; A61F 2/447; A61F 2002/2835; A61F 2002/30146; A61F 2002/30405; A61F 2002/30471; A61F 2002/30545; A61F 2002/3055; A61F 2002/30579; A61F 2002/4475; A61F 2002/4623; A61F 2002/4627; A61F 2002/3037; A61F 2002/30373; A61F 2002/30415; A61F 2002/30472; A61F 2/4465

USPC ........... 623/17.11–17.16; 606/279, 246, 329, 606/99

See application file for complete search history.

(56) References Cited

U.S. PATENT DOCUMENTS

| 5,390,683 | A  | * | 2/1995  | Pisharodi ...................... 128/898 |
| 6,039,761 | A  | * | 3/2000  | Li et al. ...................... 623/17.16 |
| 8,105,382 | B2 | * | 1/2012  | Olmos et al. ............... 623/17.15 |
| 8,317,798 | B2 | * | 11/2012 | Lim et al. ........................ 606/90 |
| 8,435,298 | B2 | * | 5/2013  | Weiman ...................... 623/17.16 |
| 8,512,407 | B2 | * | 8/2013  | Butler et al. ............... 623/17.16 |
| 2010/0174373 | A1 | * | 7/2010 | Galley et al. ............... 623/17.13 |
| 2012/0290094 | A1 | * | 11/2012 | Lim et al. ................... 623/17.16 |
| 2014/0012383 | A1 | * | 1/2014 | Triplett et al. ............. 623/17.16 |

* cited by examiner

*Primary Examiner* — Pedro Philogene
(74) *Attorney, Agent, or Firm* — Kermit D. Lopez; Luis M. Ortiz; Ortiz & Lopez, PLLC

(57) ABSTRACT

An implant apparatus and a method for spinal fusion from oblique, lateral, ALIF, PLIF, and TLIF approach. The apparatus can include an expandable implant cage and an inserter. The cage can be inserted between endplates of upper and lower vertebra using lateral, ALIF, PLIF, and/or TLIF approaches. The cage generally includes a male and female screw configuration and a cage expansion mechanism. The inserter inserts the cage in a spinal disc space and tightens the male and female screw arrangement. Once the cage is inserted to the desired position, the male portion of the screw can be tightened until final deployment of cage has been achieved. Tightening of male and female screw arrangement operates the cage expansion mechanism to expand the cage size. The cage can be inserted through a smaller surgical opening and then expanded to a full size assembly between the vertebrae.

20 Claims, 19 Drawing Sheets

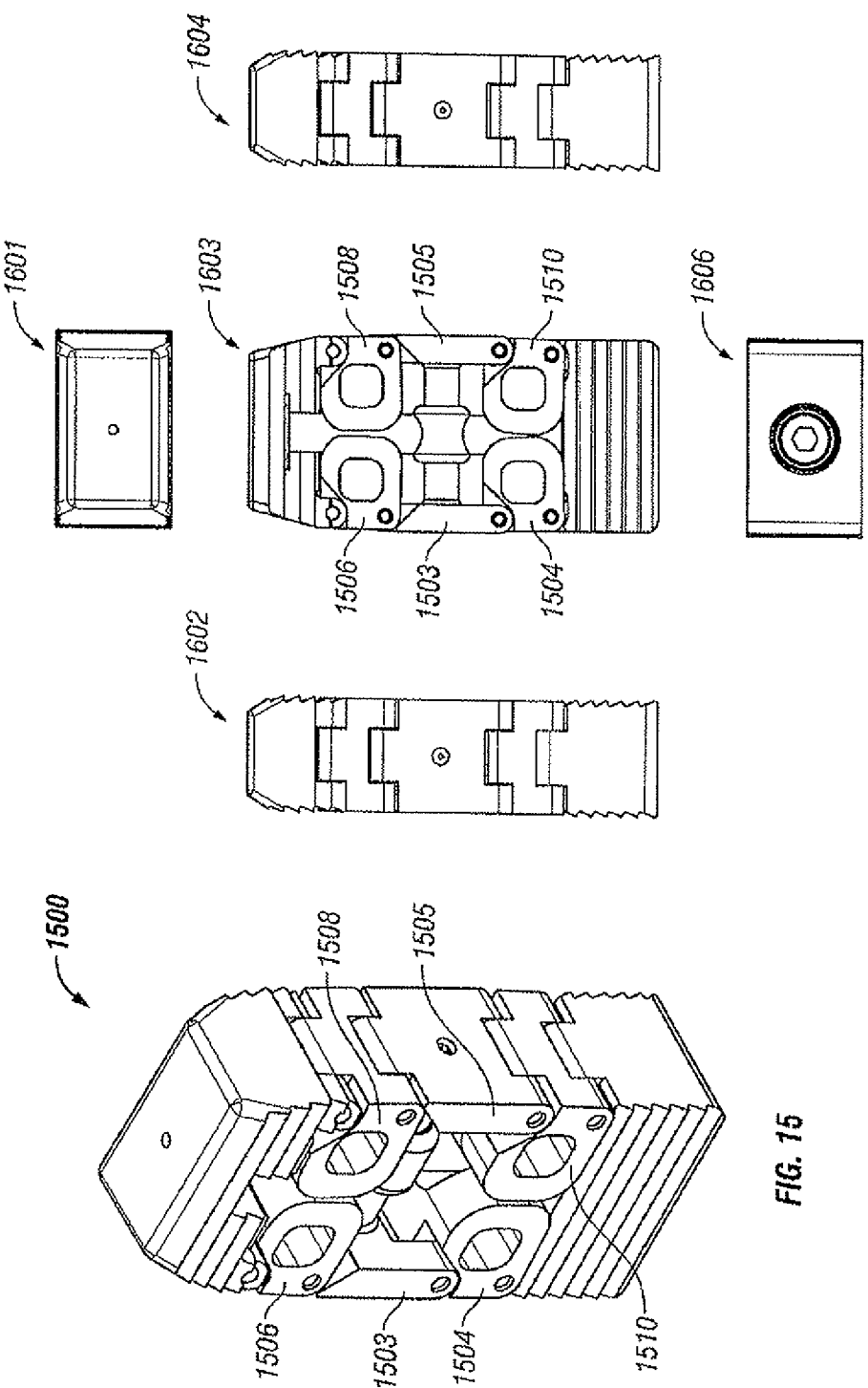

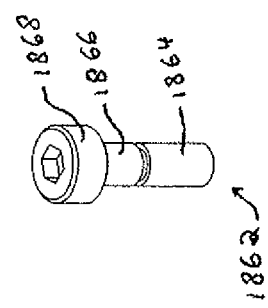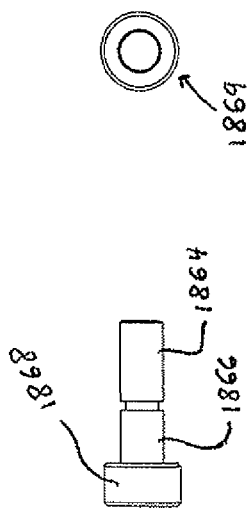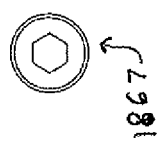
FIG. 21

IMPLANT APPARATUS AND METHOD INCLUDING TEE AND SCREW MECHANISM FOR SPINAL FUSION

CROSS-REFERENCE TO PROVISIONAL PATENT APPLICATION

This patent application claims the benefit under 35 U.S.C. §119(e) of U.S. Provisional Application Ser. No. 61/589,500 entitled, "Implant Apparatus and Method Including Tee and Screw Mechanism for Spinal Fusion," which was filed on Jan. 23, 2012 and is incorporated herein by reference in its entirety.

TECHNICAL FIELD

Embodiments are generally related to spinal implants. Embodiments also relate to the field of vertebral body spacers. Embodiments additionally relate to implanting techniques and surgical devices and components devices for spinal fusion. Embodiments are also related to cage devices and components utilized in spinal implant devices.

BACKGROUND OF THE INVENTION

In some instances, an intervertebral disc that becomes degenerated may need to be partially or fully removed from a spinal column. Intervertebral discs can degenerate due to various causes such as, for example, trauma, disease, or aging. Removal or partial removal of an intervertebral disc destabilizes the spinal column. A spinal implant may thus be inserted into a disc space created by the removal or partial removal of an intervertebral disc. The spinal implant may maintain the height of the spine and restore stability to the spine. Bone then grows from the adjacent vertebrae into the spinal implant. The bone growth fuses the adjacent vertebrae.

A spinal implant can be inserted utilizing an anterior, transforaminal, oblique, posterior or lateral spinal approach. For an anterior approach, extensive vessel retraction is often required and many vertebral levels are not readily accessible from this approach. Another approach is a posterior approach. This approach typically requires that both sides of the disc space on either side of the spinal cord be surgically exposed, which may require a substantial incision or multiple access locations, as well as extensive retraction of the spinal cord.

Yet another approach is a postero-lateral approach to the disc space. The posterior-lateral approach is employed in a posterior lumbar interbody fusion (PLIF) or transforaminal lumber interbody fusion (TLIF) procedure, which may be performed as an open technique, which requires making a larger incision along the middle of the back. Through this incision, the surgeon then cuts away, or retracts, spinal muscles and tissue to access the vertebrae and disc space. The TLIF procedure may also be performed as a minimally invasive or as an extreme lateral interbody fusion procedure that involves a retroperitoneal transpoas approach to the lumbar spine as an alternative to "open" fusion surgery. In the minimally invasive procedure, the surgeon employs much smaller incisions, avoids disrupting major muscles and tissues in the back and reduces the amount of muscle and tissue that is cut or retracted.

Anterior Lumbar Interbody Fusion (ALIF) using threaded devices such as cages and bone dowels have been in use for over ten years. Initially, threaded cages or dowels were expected to act as a stand-alone device that would promote fusion and maintain disc height without the need for posterior surgery and instrumentation of the spine. In spite of fusion rates better than 90 percent for single level fusion and 65 percent for two-level fusion, significant subsidence has been observed on follow-up X-rays at varying times following the procedure. This subsidence, or slow insinuation of the threaded devices into the vertebral bodies, has resulted in lost disc height, which in some patients has resulted in the failure to fuse and the recurrence of often very painful symptoms.

The implants may be constructed of any biocompatible materials sufficiently strong to maintain spinal distraction including, but not limited to, bone, metals, ceramics and/or polymers. Implants may be packed with bone graft or a synthetic bone graft substitute to facilitate spinal fusion. Implants may have a variety of shapes, which include, but are not limited to, threaded cylinders, unthreaded cylinders, and parallelepipeds.

A protective sleeve can be used during preparation and insertion of a spinal implant. The protective sleeve serves to protect abdominal organs, blood vessels and other tissue during a spinal implant procedure using an anterior approach. The sleeve typically extends above the surgical opening during use. The sleeve maintains distraction of the vertebrae. Also, the sleeve serves as an alignment guide for tool and implant insertion during the surgical procedure. Protective sleeves can also be used during a spinal fusion procedure using a posterior or lateral approach.

Typically, most surgical corrections of a disc space include at least a partial discectomy, which is followed by restoration of normal disc space height and, in some instances, fusion of the adjacent vertebral bodies. Restoration of normal disc space height generally involves the implantation of a spacer and fusion typically involves inclusion of bone graft or bone graft substitute material into the intervertebral disc space to create bony fusion. Fusion rods may also be employed. Some implants further provide artificial dynamics to the spine. Such techniques for achieving interbody fusion or for providing artificial disc functions are well known.

The inter-vertebral spacing (i.e., between neighboring vertebrae) in a healthy spine can be maintained via a compressible and somewhat elastic disc. The disc serves to allow the spine to move about the various axes of rotation and through the various arcs and movements required for normal mobility. The elasticity of the disc maintains spacing between the vertebrae, allowing room or clearance for compression of neighboring vertebrae, during flexion and lateral bending of the spine. In addition, the disc allows relative rotation about the vertical axis of neighboring vertebrae, allowing twisting of the shoulders relative to the hips and pelvis. Clearance between neighboring vertebrae maintained by a healthy disc is also important to allow nerves from the spinal chord to extend out of the spine, between neighboring vertebrae, without being squeezed or impinged by the vertebrae.

In situations (based upon injury or otherwise) where a disc is not functioning properly, the inter-vertebral disc tends to compress, and in doing so pressure is exerted on nerves extending from the spinal cord by this reduced inter-vertebral spacing. Various other types of nerve problems may be experienced in the spine, such as exiting nerve root compression in neural foramen, passing nerve root compression. A few medical procedures have been devised to alleviate such nerve compression and the pain that results from nerve pressure. Many of these procedures revolve around attempts to prevent the vertebrae from moving too close to each other by surgically removing an improperly functioning disc and replacing it with a lumber interbody fusion (LIF) device. Although prior interbody devices, including LIF cage devices, may be effective at improving patient condition, the vertebrae of the spine, body organs, the spinal cord, other nerves, and other adjacent bodily structures make obtaining surgical access to the location between the vertebrae where the LIF cage is to be installed difficult.

In case of lateral approach, it would be desirable to reduce the size of the LIF/VBR cage to minimize the size for the required surgical opening for installation of the LIF/VBR cage, while maintaining high strength, durability and reliability of the LIF/VBR cage device. Instruments and lateral implants are not necessarily suited to efficiently distract the disc space without damaging the adjacent endplates. In an effort to address the foregoing difficulties, it is believed that the implant device for spinal fusion from lateral approach, as discussed herein, can address many of the problems with traditional lateral implants.

BRIEF SUMMARY

The following summary is provided to facilitate an understanding of some of the innovative features unique to the disclosed embodiment and is not intended to be a full description. A full appreciation of the various aspects of the embodiments disclosed herein can be gained by taking the entire specification, claims, drawings, and abstract as a whole.

It is, therefore, one aspect of the disclosed embodiments to provide for spinal implants.

It is another aspect of the disclosed embodiments to provide for vertebral body spacers.

It is yet another aspect of the disclosed embodiments to provide for implanting techniques and device for spinal fusion from lateral approach.

It is also an aspect of the disclosed embodiments to provide a spinal implant device with a cage apparatus that includes four boxes or cavities and in which the autograft, allograft or scaffold material does not migrate when such a cage apparatus is deployed or expanded.

It is a further aspect of the disclosed embodiments to provide for an inner working male and female Tee component and screw mechanism that contains a center control post that allows a user to open and close the disclosed system/apparatus in a controlled manner.

The aforementioned aspects and other objectives and advantages can now be achieved as described herein. An implant apparatus and a method for spinal fusion from oblique, lateral, ALIF, PLIF, and TLIF approach are disclosed. The apparatus can be configured to include an expandable implant cage and an inserter. The cage can be inserted between endplates of upper and lower vertebra using an oblique, lateral, ALIF, PLIF, and/or TLIF approach. The cage generally includes a male and female screw configuration and a cage expansion mechanism. The inserter inserts the cage in a spinal disc space and tightens the male and female screw arrangement. Once the cage is inserted to the desired position, viewed by X-ray you will begin to tighten the male portion of the screw in the device, and continue to tighten until final deployment of cage has been achieved. This provides a much greater footprint that allows the device to reach the cortical ring or apophyseal ring of the vertebral body. Tightening of male and female screw arrangement operates the cage expansion mechanism to expand the cage size. The cage can be inserted through a smaller surgical opening and then expanded to a full size assembly between the vertebrae. The disclosed spinal implant device including the cage with its four boxes or cavities allows the autograft, allograft or scaffold material to not migrate when the cage is deployed or expanded. Such a spinal fusion apparatus includes an inner working male and female Tee component and screw mechanism that contains a center control post that allows a user to open and close the disclosed system/apparatus in a controlled manner.

BRIEF DESCRIPTION OF THE DRAWINGS

The accompanying figures, in which like reference numerals refer to identical or functionally similar elements throughout the separate views and which are incorporated in and form a part of the specification, further illustrate the disclosed embodiments and, together with the detailed description of the invention, serve to explain the principles of the disclosed embodiments.

FIG. 15 illustrates a perspective view of an implant apparatus for spinal fusion, in accordance with another embodiment;

FIG. 16 illustrates a left side view, a front view, a right side view, a bottom view and a top view of the implant cage of the apparatus depicted in FIG. 15;

FIG. 21 illustrates a diagram of a male screw post, which can be employed for deployment (open/close) of the cage apparatus disclosed herein, in accordance with an alternative embodiment.

DETAILED DESCRIPTION

The particular values and configurations discussed in these non-limiting examples can be varied and are cited merely to illustrate at least one embodiment and are not intended to limit the scope thereof.

Figure 1:
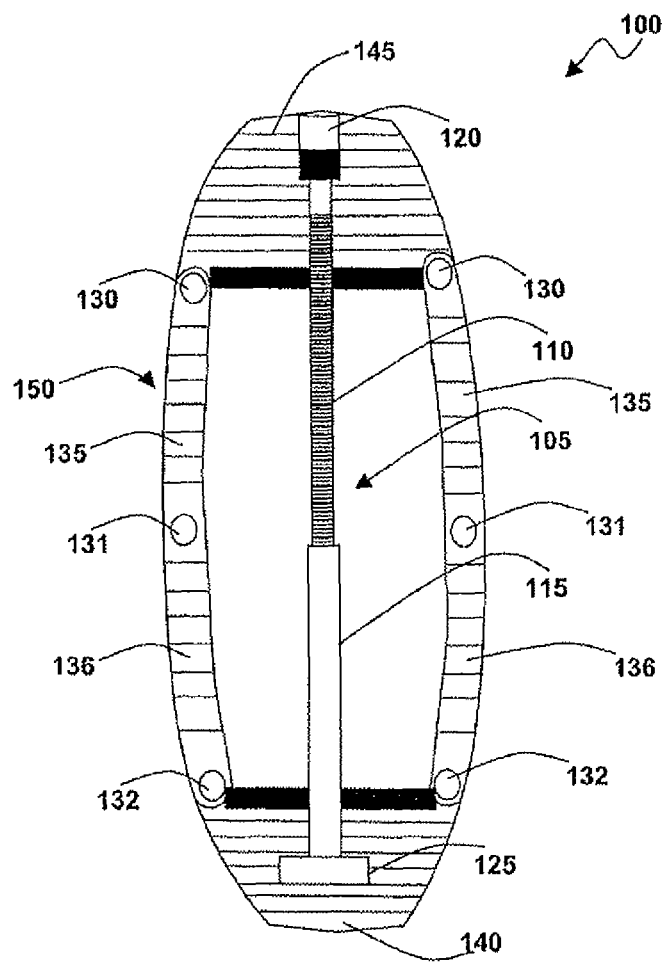
FIG. 1 illustrates a top view of an implant cage utilized for spinal fusion, in accordance with the disclosed embodiments.

FIG. 1 illustrates a top view of an implant cage apparatus 100 utilized for spinal fusion, in accordance with the disclosed embodiments. Note that as utilized herein the term "spinal fusion" can include, for example, lumbar fusion and other procedures. The cage apparatus 100 includes a male and female screw arrangement 105, a cage expansion mechanism 150. A head 125 of a male screw 115 and a head 120 of a female screw 110 are positioned on the front side 140 and back side 145 of the cage apparatus 100 respectively. The cage expansion mechanism 150 includes pins 130, 131 and 132 and hinges 135 and 136. The hinges 135 and 136 are generally connected by a common pin 131.

Figure 2:
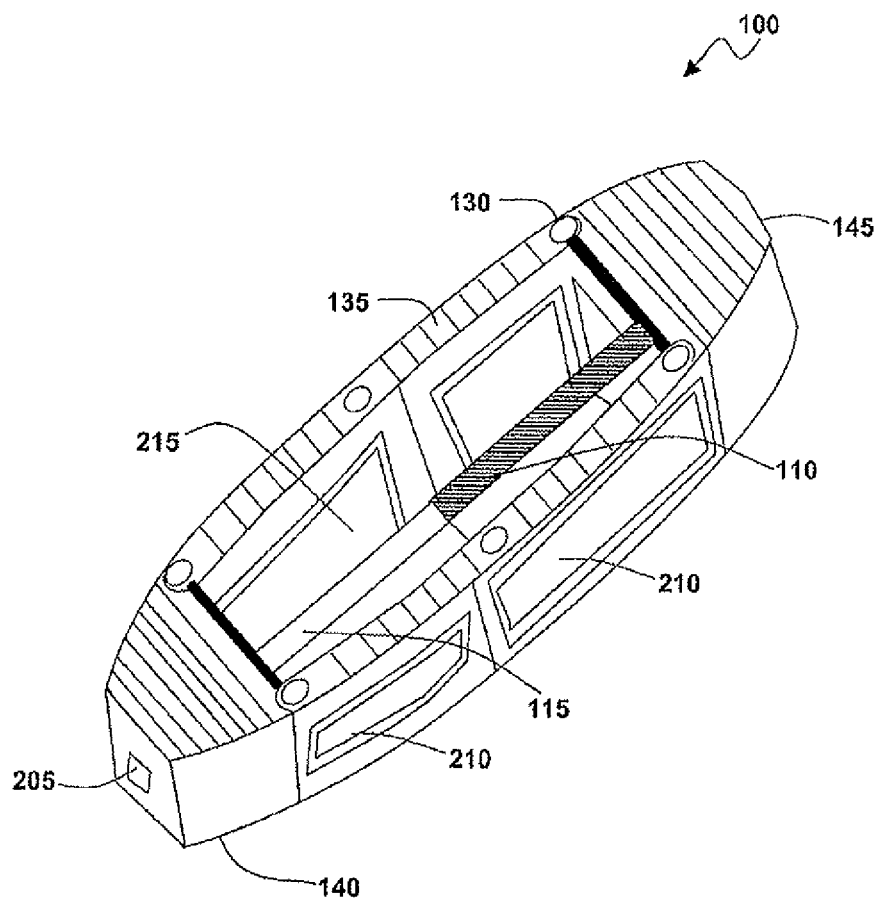
FIG. 2 illustrates a perspective view of the implant cage of FIG. 1, in accordance with the disclosed embodiments.
Figure 3:
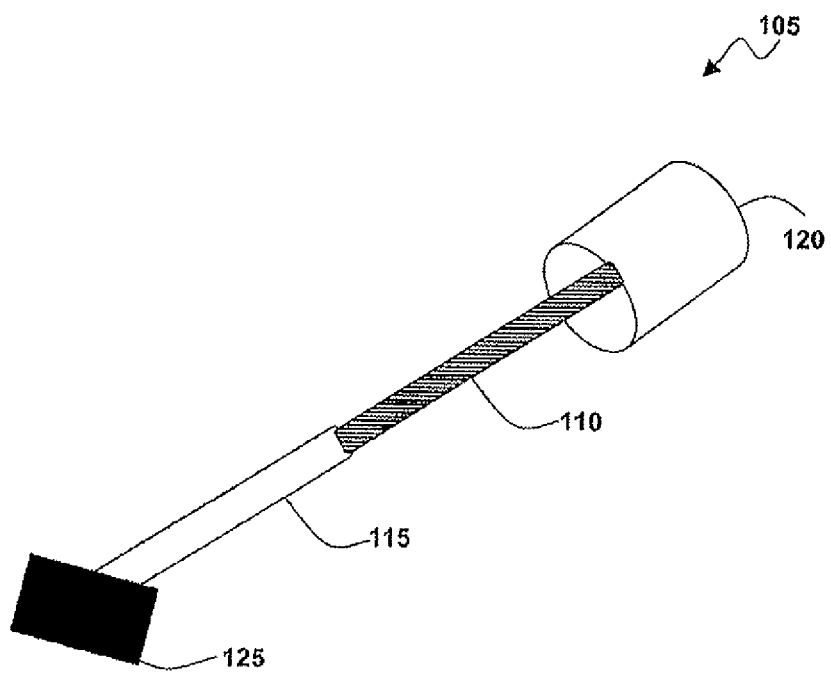
FIG. 3 illustrates a perspective view of a male and female screw arrangement of FIG. 1, in accordance with the disclosed embodiments.

FIG. 2 illustrates a perspective view of the implant cage apparatus 100 of FIG. 1, in accordance with the disclosed embodiments. An aperture 210 allows the healing material to flow in and out of a cavity 215. The cage apparatus 100 can be inserted into the spinal disc space through a port 205 on the front side 140. FIG. 3 illustrates a perspective view of the male and female screw arrangement 105 utilized in FIG. 1, in accordance with the disclosed embodiments. When the male and female screw arrangement 105 is tightened by an inserter (not shown), the cage expansion mechanism 150 expands the cage apparatus 100 and increases it size.

Figure 4:
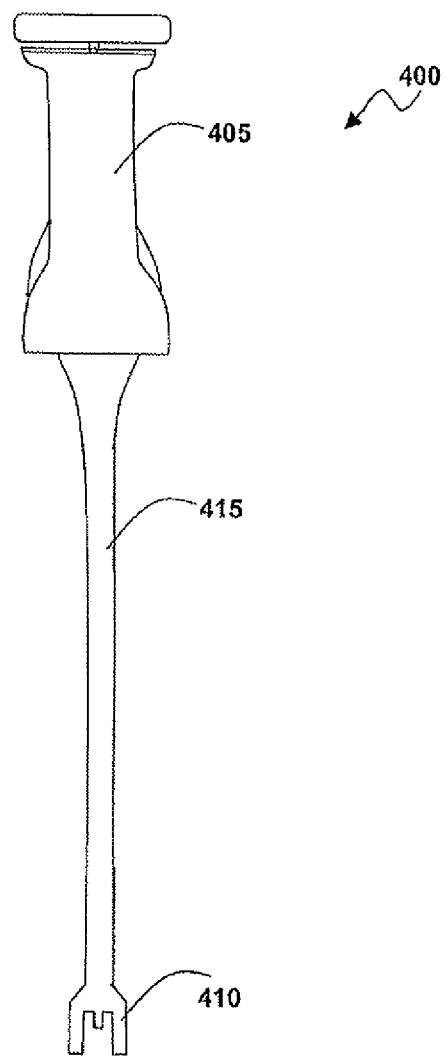
FIG. 4 illustrates a perspective view of an inserter utilized in implantation process, in accordance with disclosed embodiments.

FIG. 4 illustrates a perspective view of an inserter 400 that can be utilized in spinal implantation process, in accordance with disclosed embodiment. The inserter includes a handle 405, a coupling arrangement 410 and a shaft 415. The inserter 400 is utilized for inserting the cage into spinal disc space (not shown). Inserter 400 is also utilized for tightening the male and female screw arrangement 105. Tightening of the male and female screw arrangement 105 expands the size of the cage apparatus 100.

Figure 5:
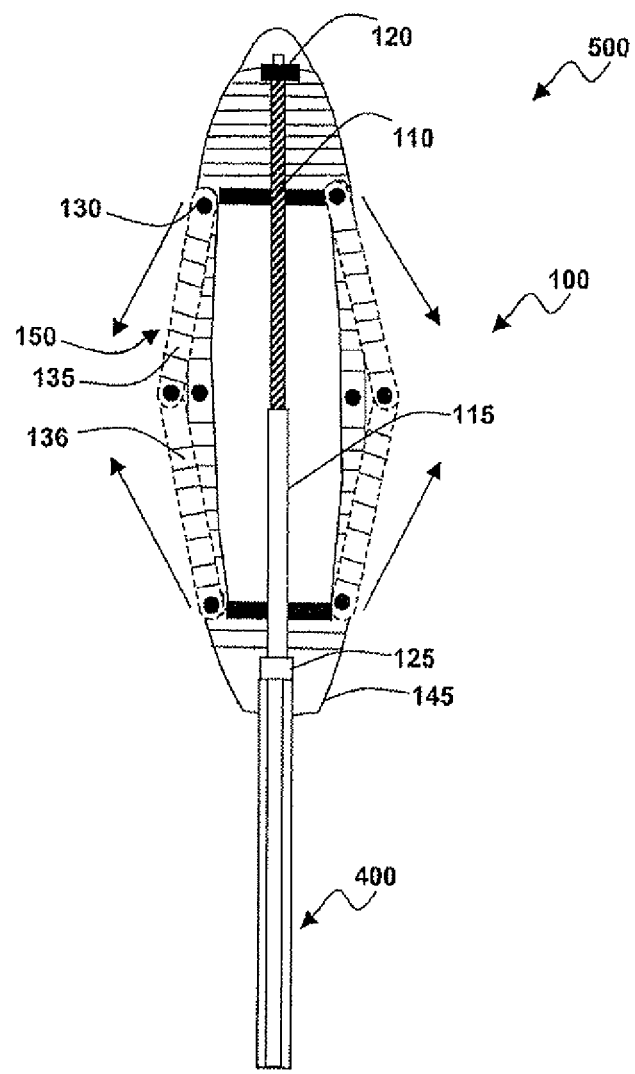
FIG. 5 illustrates a perspective view of the implant device including the implant cage of FIG. 1 and the inserter of FIG. 4, in accordance with the disclosed embodiments.

FIG. 5 illustrates a perspective view of the implant device 500 after expansion by utilizing the inserter 400 of FIG. 4, in accordance with the disclosed embodiments. The implant device 500 includes the cage apparatus 100 and inserter 400. Note that the hinges 135 and 136 can be configured to stretch generally outside the cage and thus increase the size of the cage apparatus 100. Note also that the cage apparatus 100 (also referred to sometimes as simply "the cage") can be inserted through a smaller surgical opening and then expanded to a full size assembly between the vertebrae. The disclosed spinal device including the cage apparatus 100 with its four boxes or cavities allows the autograft, allograft or scaffold material to not migrate when the cage is deployed or expanded. Such a spinal fusion apparatus includes an inner working male and female Tee component and screw mechanism that contains a center control post that allows a user to open and close the disclosed system/apparatus in a controlled manner.

Figure 6:
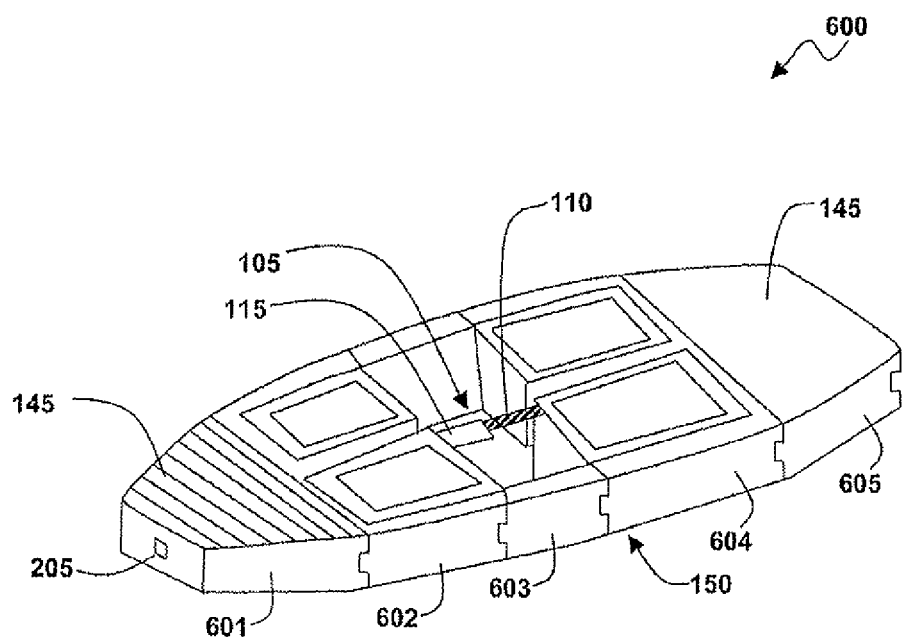
FIG. 6 illustrates a perspective view of an implant cage, in accordance with an alternative embodiment.
Figure 7:
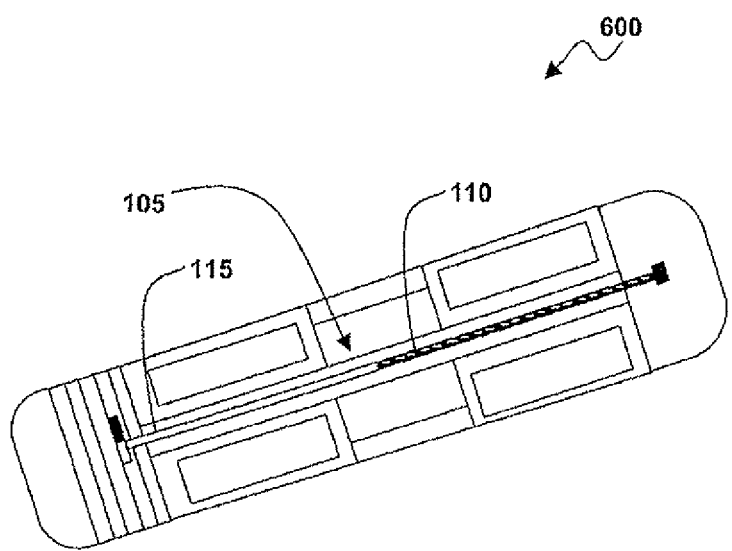
FIG. 7 illustrates a top view of the implant cage of FIG. 6, in accordance with an alternative embodiment.
Figure 8:
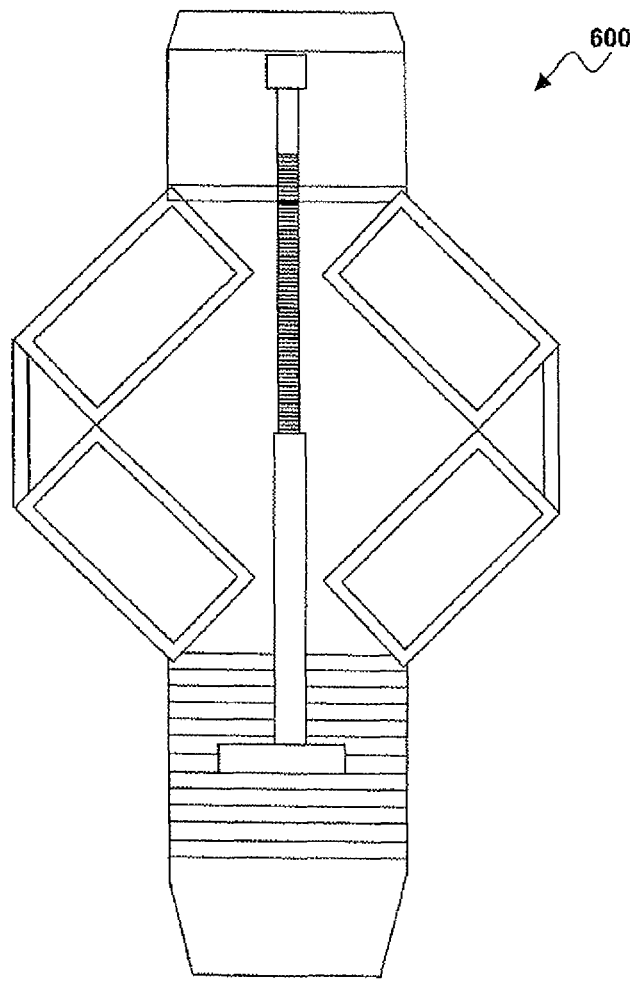
FIG. 8 illustrates a perspective view of the implant cage of FIG. 6 after expansion, in accordance with an alternative embodiment.
Figure 9:
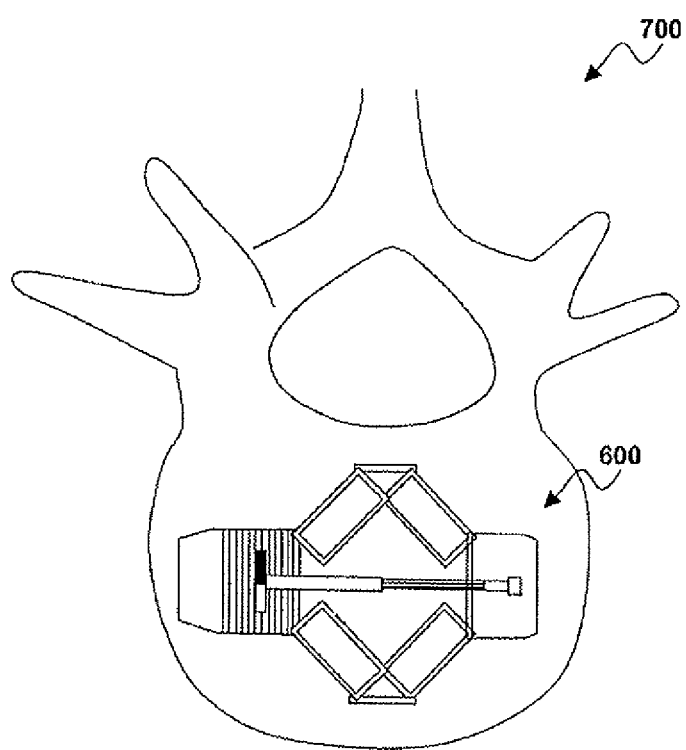
FIG. 9 illustrates a perspective view of a vertebral endplate with the implant cage of FIG. 8, in accordance with an alternative embodiment.

FIG. 6 illustrates a perspective view of an implant cage 600, in accordance with an alternative embodiment. The cage expansion mechanism 150 includes expandable compartments 601, 602, 603, 604 and 605. Upon tightening the male and female screw arrangement 105, the compartments 601, 602, 603, 604 and 605 stretches and increases the size of the cage 600. FIG. 7 illustrates a top view of implant cage 600 of FIG. 6, in accordance an alternative embodiment. FIG. 8 illustrates a perspective view of implant cage 600 of FIG. 6 after expansion, in accordance with an alternative embodiment. FIG. 9 illustrates a perspective view of vertebral endplate 700 with the implant cage 600 of FIG. 8, in accordance with an alternative embodiment.

Figure 10:
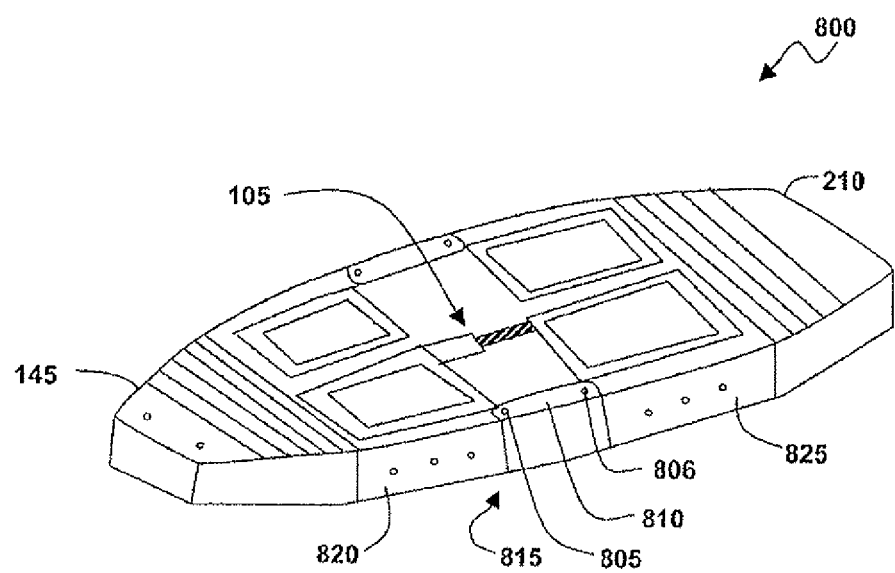
FIG. 10 illustrates a perspective view of an implant cage, in accordance with an alternative embodiment.
Figure 11:
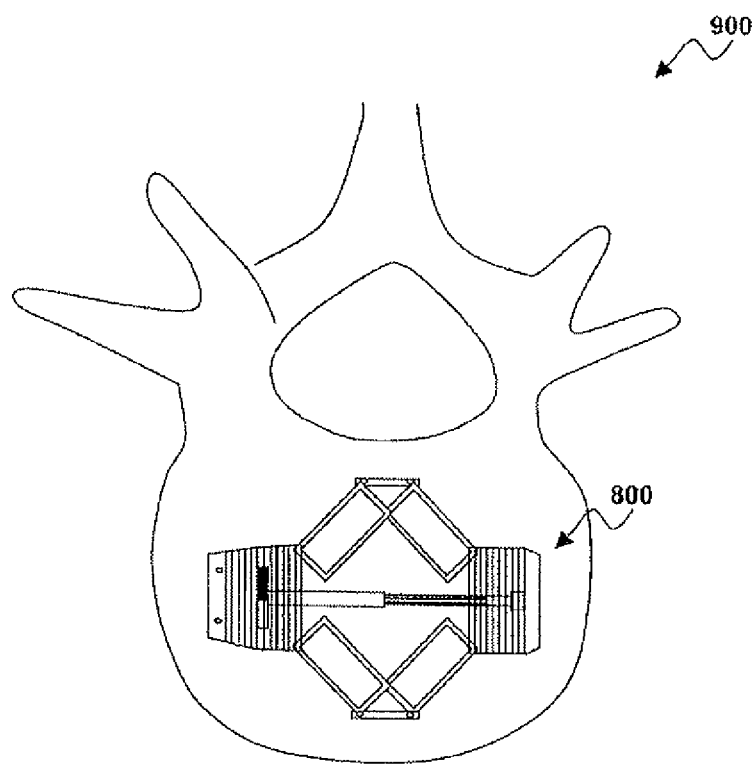
FIG. 11 illustrates a perspective view of a vertebral endplate with the implant cage of FIG. 10, in accordance with an alternative embodiment.

FIG. 10 illustrates a perspective view of an implant cage 800, in accordance with an alternative embodiment. The expansion mechanism 815 includes pins 805 and 806, hinge 810 and a set of compartments 820 and 825. The expansion mechanism 815 stretches and increases the cage size upon tightening the male and female screw arrangement 105. FIG. 11 illustrates a perspective view of vertebral endplate 900 with the implant cage 800 of FIG. 10, in accordance with an alternative embodiment.

Figure 12:
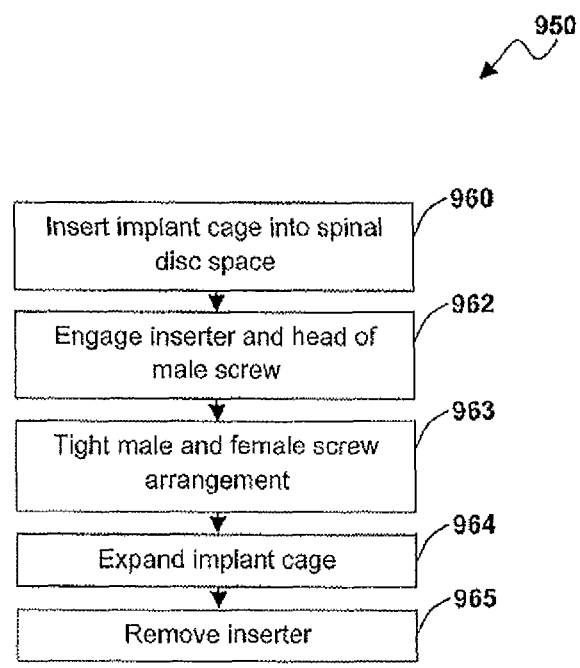
FIG. 12 illustrates a high level flow chart depicting implantation process for spinal fusion from lateral approach, in accordance with the disclosed embodiments.

FIG. 12 illustrates a high-level flow chart 950 depicting implantation process for spinal fusion from lateral approach, in accordance with the disclosed embodiments. As illustrated at block 960 the inserter is utilized for inserting cage into the spinal disc space using lateral approach. Then, the inserter is engaged with the male screw head as indicated at block 962. As depicted at block 963, the male and female screw arrangement can be tightened utilizing the inserter discussed herein. According to the required space between the endplates of upper and lower vertebra, the cage can be expanded as illustrated at block 964. Finally, the inserter is removed as described at block 965.

Figure 13:
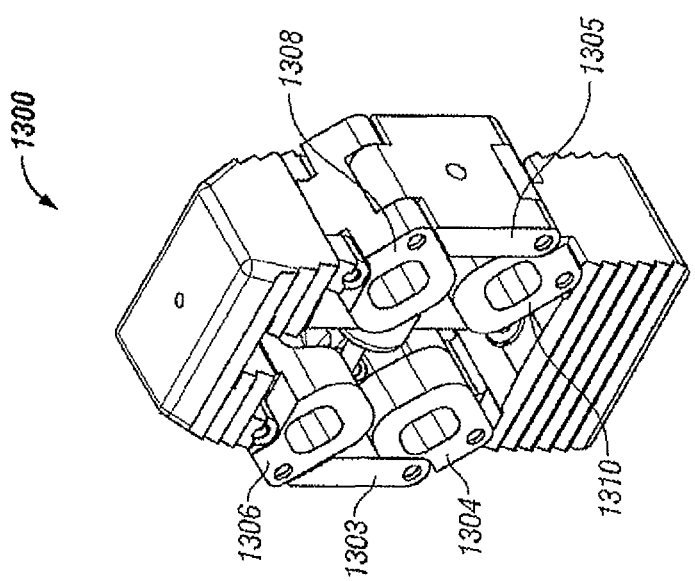
FIG. 13 illustrates a perspective view of an implant apparatus for spinal fusion, in accordance with another embodiment.

FIG. 13 illustrates a perspective view of an implant apparatus 1300 for spinal fusion, in accordance with another embodiment. As shown in FIG. 13, moveable sections 1304, 1306, 1308, 1319 are illustrated. Section 1303 links section 1306 and 1304 to one another, while section 1305 links sections 1308 and 1310 in the configuration shown in FIG. 13.

Figure 14:
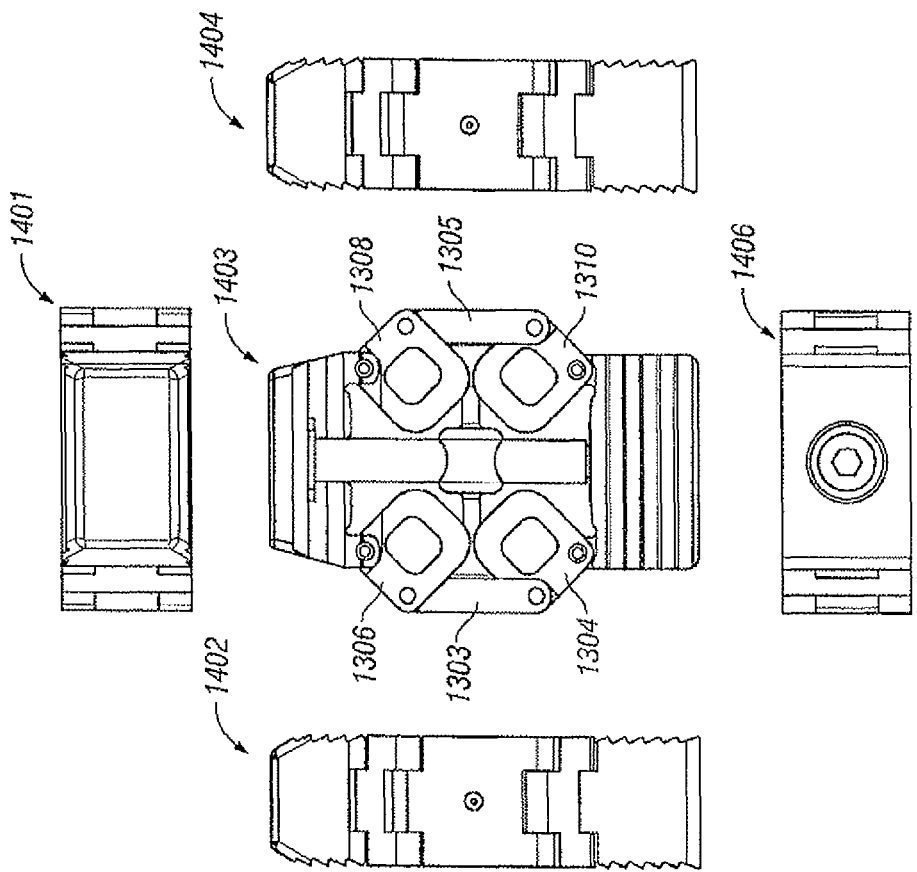
FIG. 14 illustrates a left side view, a front view, a right side view, a bottom view and a top view of the implant cage of the apparatus depicted in FIG. 13.

FIG. 14 illustrates a left side view 1402, a front view 1403, a right side view 1404, a bottom view 1406 and a top view 1401 of the implant cage of the apparatus 1300 depicted in FIG. 13. Note that in FIGS. 13-14, similar or like parts are general indicated by identical reference numerals.

FIG. 15 illustrates a perspective view of an implant apparatus 1500 for spinal fusion, in accordance with another embodiment. As shown in FIG. 15, moveable sections 1506 and 1504 connect to section 1503, and sections 1508 and 1510 are linked via section 1505.

Figure 17:
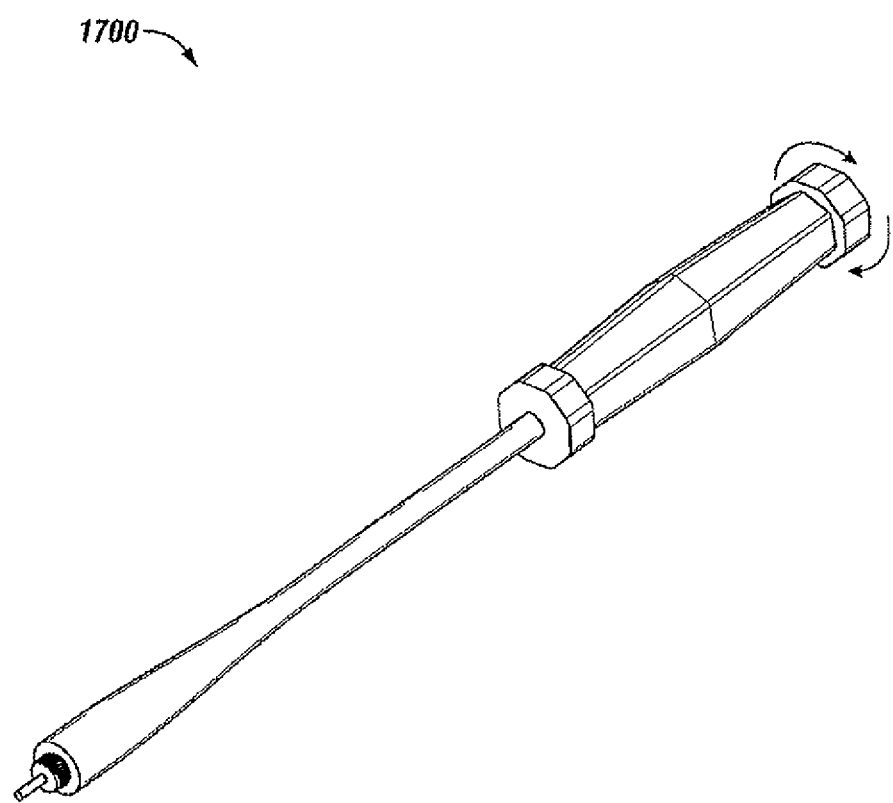
FIG. 17 illustrates a perspective view of an inserter device that can be utilized in accordance with the disclosed embodiments.

FIG. 16 illustrates a left side view 1602, a front view 1603, a right side view 1604, a bottom view 1606 and a top view 1601 of the implant cage of the apparatus depicted in FIG. 15. FIG. 17 illustrates a perspective view of an inserter 1700 that can be utilized in accordance with the disclosed embodiments. The inserter 1700 shown in FIG. 16 thus represents an alternative embodiment (e.g. a variation to inserter 400) for use in spinal implantation processes.

FIG. 17 illustrates a perspective view of an alternative inserter tool 1700, which can be utilized in a spinal implantation process, in accordance with an alternative embodiment. The tool 1700 is an embodiment alternative to the inserter depicted in FIG. 4.

Figure 18:
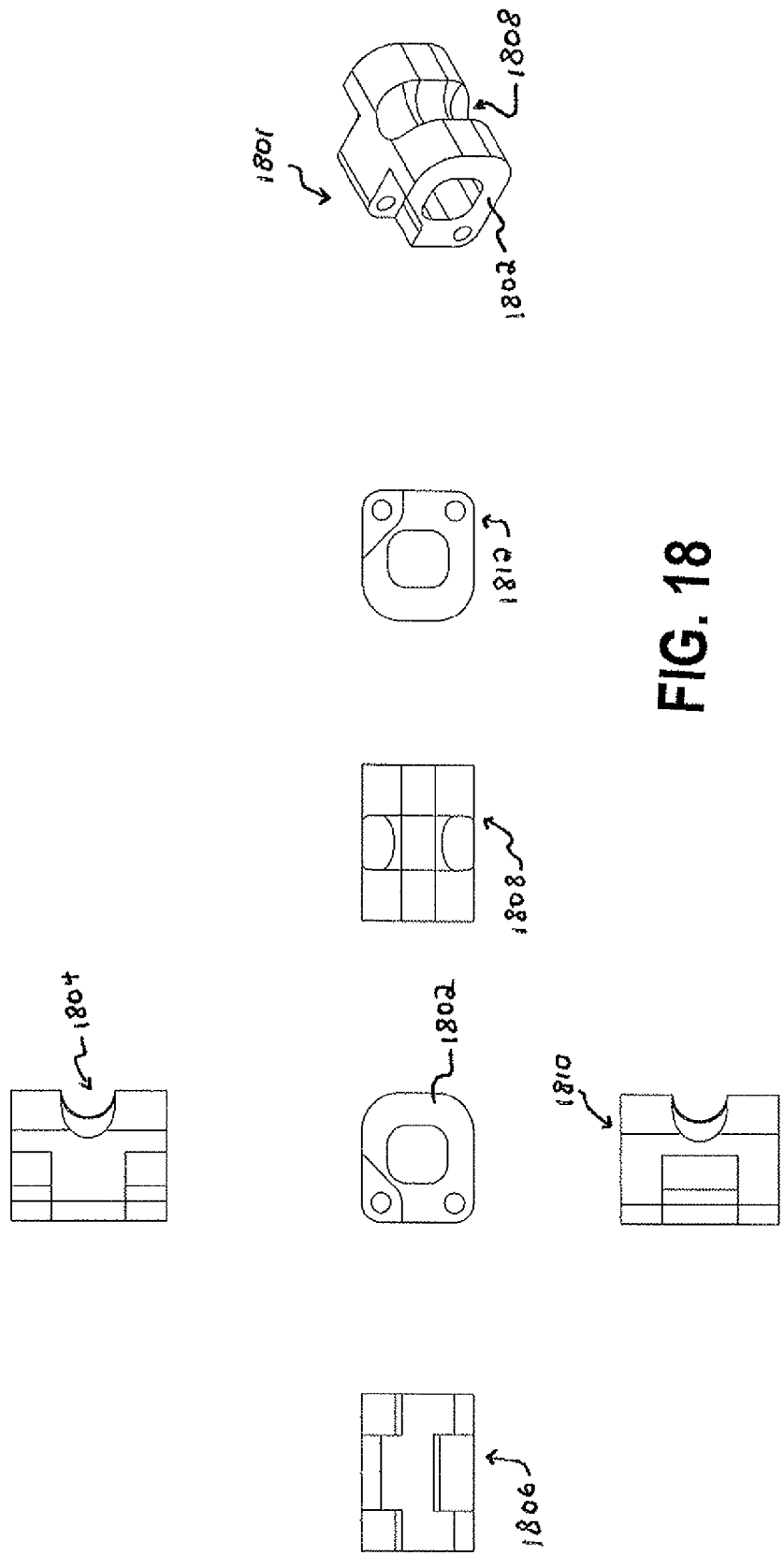
FIG. 18 illustrates a diagram depicting varying views of at least one graft portion of the cage apparatus disclosed herein, in accordance with an alternative embodiment.

FIG. 18 illustrates a diagram 1800 depicting varying views of at least one graft portion 1801 of the cage apparatus disclosed herein, in accordance with an alternative embodiment. The graft portion 1801 is analogous to the moveable sections

1304, 1306, 1308, 1319 discussed earlier herein. Graft portion 1801 is thus one of four graft windows. Each graft portion or graft window 1801 can include, for example, an internal channel such as internal channel 1808 for the male/female mechanism described herein. As shown in FIG. 18, a top section 1802 of the graft portion 1801 is shown with respect to side portions 1804, 1806, 1808, 1810 and rear section 1812.

Figure 19:
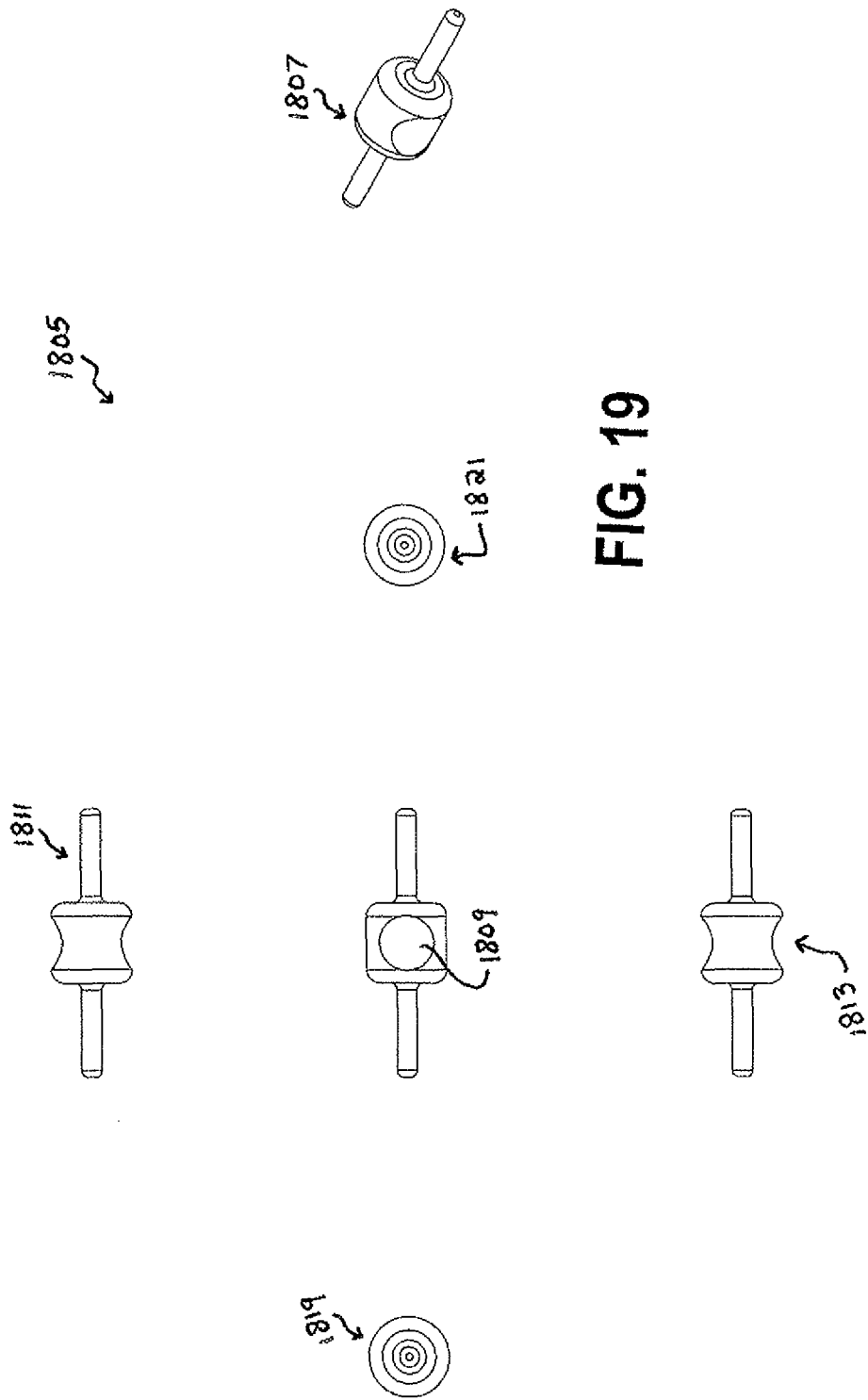
FIG. 19 illustrates a diagram of a post, which can assist in the opening or closing of the cage apparatus discussed herein, in accordance with an alternative embodiment.

FIG. 19 illustrates a diagram 1805 of a post 1807, which can assist in the opening or closing of the cage apparatus discussed herein, in accordance with an alternative embodiment. Respective top and bottom portions 1819 and 1821 of the post 1807 are shown in FIG. 15. Side views 1811 and 1813 of post 1807 are also shown in FIG. 19. A central portion 1809 of the post 1807 is also shown in FIG. 19.

Figure 20:
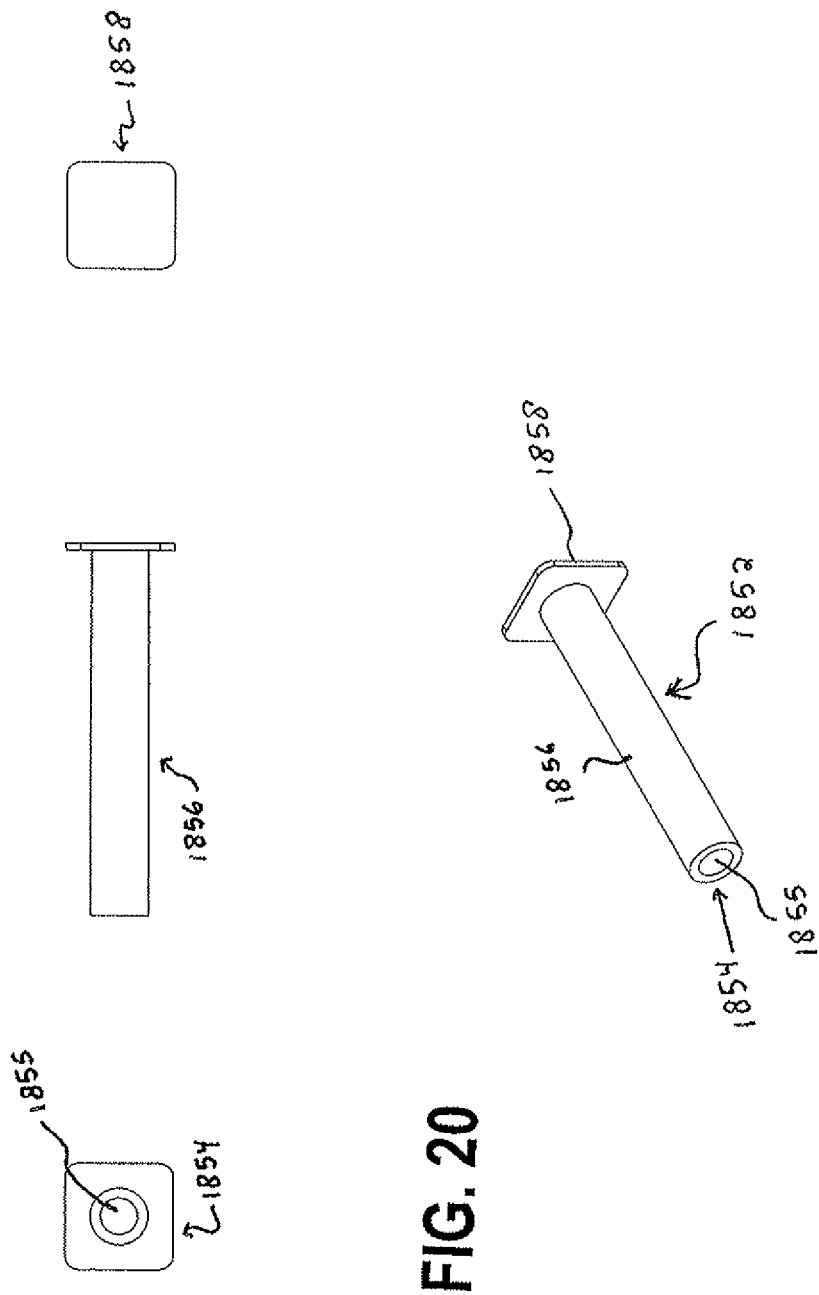
FIG. 20 illustrates a diagram of a female post, which can be employed for deployment (open/close) of the cage apparatus disclosed herein, in accordance with an alternative embodiment.

FIG. 20 illustrates diagram 1850 of a female post 1852, which can be employed for deployment (open/close) of the cage apparatus disclosed herein, in accordance with an alternative embodiment. A top portion 1854 with a circular end 1855 and a bottom portion 1858 are shown in FIG. 20, along with the elongated central portion 1856 of the female post 1852.

FIG. 21 illustrates a diagram 1860 of a male screw post 1862, which can be employed for deployment (open/close) of the cage apparatus disclosed herein, in accordance with an alternative embodiment. The post 1862 includes a top 1868, central portion 1866 and a bottom portion 1864. A top view 1867 of the post 1862 is shown in FIG. 21 along with a bottom view 1869 of the post 1862.

Based on the foregoing, it can be appreciated that an implant apparatus and a method for spinal fusion from oblique, lateral, ALIF, PLIF, and/or TLIF approaches are disclosed. The apparatus/device can be configured to include an expandable implant cage and an inserter. The cage can be inserted between endplates of upper and lower vertebra using oblique, lateral, ALIF, PLIF, and TLIF approach. The cage generally includes a male and female screw configuration and a cage expansion mechanism. The inserter inserts the cage in a spinal disc space and tightens the male and female screw arrangement. Once the cage is inserted to the desired position, viewed by X-ray you will begin to tighten the male portion of the screw in the device, and continue to tighten until final deployment of cage has been achieved. This provides a much grater footprint that allows the device to reach the cortical ring or apophyseal ring of the vertebral body. Tightening of male and female screw arrangement operates the cage expansion mechanism to expand the cage size. The cage can be inserted through a smaller surgical opening and then expanded to a full size assembly between the vertebrae.

Based on the foregoing, it can be appreciated that various embodiments are disclosed, including preferred and alternative embodiments. For example, in an embodiment, an implant apparatus for spinal fusion can include an expandable implant cage positioned between endplates of upper and lower vertebra comprising a male and female screw arrangement and a cage expansion mechanism, wherein the cage expansion mechanism expands the cage size on tightening the male and female screw arrangement; and an inserter for inserting the cage in a spinal disc space that maintains a handle, a shaft and a coupling arrangement, wherein the inserter is operated to engage the coupling arrangement with the male and female screw arrangement and to tighten the male and female screw arrangement.

In some embodiments, the cage expansion mechanism can comprise a pin and hinge configuration. In other embodiments, the cage expansion mechanism can comprise a cage compartment configuration. In yet other embodiments, the cage expansion mechanism can comprise a combination of a cage compartment configuration and a pin and hinge configuration. In still other embodiments, the disclosed cage expansion mechanism can be positioned on at least one sidewall of the cage. In some embodiments, the disclosed spinal fusion can be an oblique approach. In other embodiments, the spinal fusion can be a lateral approach. In yet other embodiments, the spinal fusion can be an ALIF approach, a PLIF approach, or a TLIF approach.

In another embodiment, an implant apparatus for spinal fusion can include, for example, an expandable implant cage positioned between endplates of upper and lower vertebra comprising a male and female screw arrangement and a cage expansion mechanism, wherein the cage expansion mechanism expands the cage size on tightening the male and female screw arrangement. Such an apparatus can also include an inserter for inserting the cage in a spinal disc space that maintains a handle, a shaft and a coupling arrangement, wherein the inserter is operated to engage the coupling arrangement with the male and female screw arrangement and to tighten the male and female screw arrangement. Additionally, in such an apparatus, the cage expansion mechanism can comprise at least one of: a pin and hinge configuration, a cage compartment configuration, or a combination of the cage compartment configuration and the pin and hinge configuration. In an alternative embodiment of such an apparatus, the cage expansion mechanism can be positioned on at least one sidewall of the cage. In yet another embodiment of such an apparatus, the spinal fusion can be, for example, a lateral approach, an ALIF approach, a PLIF approach, a TLIF approach and/or an oblique approach.

In still another embodiment, a method for spinal fusion may be implemented, which includes, for example, the steps of locating an expandable implant cage between endplates of upper and lower vertebra comprising a male and female screw arrangement and a cage expansion mechanism, wherein the cage expansion mechanism expands the cage size on tightening the male and female screw arrangement; providing an inserter for inserting the cage in a spinal disc space that maintains a handle, a shaft and a coupling arrangement; and operating the inserter to engage the coupling arrangement with the male and female screw arrangement and to tighten the male and female screw arrangement.

In another embodiment of such a method, a step may be implemented for positioning the cage expansion mechanism on at least one sidewall of the cage. In other embodiments of such a method, a step may be implemented for configuring the cage expansion mechanism to comprise at least one of: a pin and hinge configuration; a cage compartment configuration; or a combination of the cage compartment configuration and the pin and hinge configuration.

In a preferred embodiment, with respect to the aforementioned cage and four boxes or cavities thereof, the autograft, allograft or scaffold material will not migrate when the cage is deployed or expanded. Additionally, the inner working male and females Tee and screw mechanism that has the center control post, allows the user to open and close in a controlled manner, the system/apparatus herein.

It will be appreciated that variations of the above disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. An implant apparatus for spinal fusion, said apparatus comprising:
   an expandable implant cage capable of being positioned between endplates of upper and lower vertebra of a body, said expandable implant cage comprising a male and female screw arrangement and a cage expansion mechanism, wherein said cage expansion mechanism expands a size of said cage on tightening of said male and female screw arrangement, said cage expansion mechanism having four separate and expandable cage graft containment compartments connected by a common pin and having respective cavities therein for maintaining preloaded autograph material, allograft material or scaffold material;
   an inserter for inserting said cage in a spinal disc space that maintains a handle, a shaft and a coupling arrangement, wherein said inserter is operated to engage said coupling arrangement with said male and female screw arrangement and to tighten said male and female screw arrangement; and
   wherein said cage expands in foot print rather than height to prevent said autograft material, said allograft material or said scaffold material from migrating when said cage is deployed or expanded.

2. The apparatus of claim 1 wherein said male and female screw arrangement comprises an inner working male and female Tee component and screen mechanism that includes a center control post that allows for opening and closing of said implant apparatus in a controlled manner.

3. The apparatus of claim 2 wherein said expandable implant cage apparatus is operable from an oblique approach.

4. The apparatus of claim 2 wherein said expandable implant cage apparatus is operable from a lateral approach.

5. The apparatus of claim 2 wherein said expandable implant cage apparatus is operable from an ALIF approach.

6. The apparatus of claim 2 wherein said expandable implant cage apparatus is operable from a PLIF approach.

7. The apparatus of claim 2 wherein said expandable implant cage apparatus is operable from a TLIF approach.

8. An implant apparatus for spinal fusion, said apparatus comprising:
   an expandable implant cage capable of being positioned between endplates of upper and lower vertebra of a body, said expandable implant cage comprising a male and female screw arrangement and a cage expansion mechanism, wherein said cage expansion mechanism expands a size of said cage on tightening of said male and female screw arrangement, said cage expansion mechanism having four separate and expandable cage graft containment compartments connected by a common pin and having respective cavities therein for maintaining preloaded autograph material, allograft material or scaffold material; and
   an inserter for inserting said cage in a spinal disc space that maintains a handle, a shaft and a coupling arrangement, wherein said inserter is operated to engage said coupling arrangement with said male and female screw arrangement and to tighten said male and female screw arrangement.

9. The apparatus of claim 8 wherein said cage prevents autograft material, allograft material or scaffold material from migrating when said cage is deployed or expanded.

10. The apparatus of claim 8 wherein said male and female screw arrangement comprises an inner working male and female Tee component and screen mechanism that includes a center control post that allows for opening and closing of said implant apparatus in a controlled manner.

11. The apparatus of claim 9 wherein said male and female screw arrangement comprises an inner working male and female Tee component and screen mechanism that includes a center control post that allows for opening and closing of said implant apparatus in a controlled manner.

12. The apparatus of claim 11 wherein said expandable implant cage apparatus is operable from an oblique approach.

13. The apparatus of claim 11 wherein said expandable implant cage apparatus is operable from a lateral approach.

14. The apparatus of claim 11 wherein said expandable implant cage apparatus is operable from an ALIF approach.

15. The apparatus of claim 11 wherein said expandable implant cage apparatus is operable from a PLIF approach.

16. The apparatus of claim 11 wherein said expandable implant cage apparatus is operable from a TLIF approach.

17. An implant method for spinal fusion, said method comprising:
   positioning an expandable implant cage between endplates of upper and lower vertebra comprising a male and female screw arrangement and a cage expansion mechanism having four separate and expandable cage graph containment compartments connected by a common pin and having respective cavities therein for maintaining grafting material, wherein said cage expansion mechanism expands said cage in footprint rather than height to maintain said grafting material therein upon tightening of said male and female screw arrangement; and
   inserting, via an inserter, said cage in a spinal disc space that maintains a handle, a shaft and a coupling arrangement, wherein said inserter is operated to engage said coupling arrangement with said male and female screw arrangement and to tighten said male and female screw arrangement and to expand said cage in foot print rather than height to maintain said grafting material within said cage and from migrating when said cage is deployed or expanded.

18. The method of claim 17 wherein said cage prevents autograft material, allograft material or scaffold material from migrating when said cage is deployed or expanded.

19. The method of claim 8 wherein said male and female screw arrangement comprises an inner working male and female Tee component and screen mechanism that includes a center control post that allows for opening and closing of said implant apparatus in a controlled manner.

20. The method of claim 18 wherein said expandable implant cage apparatus is operable from at least one of an oblique approach, a lateral approach, an ALIF approach, a PLIF approach, and a TLIF approach.

* * * * *